United States Patent [19]

Obenaus et al.

[11] 4,219,678
[45] Aug. 26, 1980

[54] PROCESS FOR PREPARING PURE METHYL TERT.-BUTYL ETHER

[75] Inventors: Fritz Obenaus; Wilhelm Droste, both of Marl; Wolf Streubel, Dorsten; Michael Zölffel; Wolfgang Müller, both of Marl, all of Fed. Rep. of Germany

[73] Assignee: Chemische Werke Hüls A G, Marl, Fed. Rep. of Germany

[21] Appl. No.: 974,550

[22] Filed: Dec. 29, 1978

Related U.S. Application Data

[63] Continuation of Ser. No. 810,878, Jun. 28, 1977, abandoned.

[30] Foreign Application Priority Data

Jul. 2, 1976 [DE] Fed. Rep. of Germany ....... 2629769

[51] Int. Cl.$^2$ .................... C07C 41/12; C07C 41/00
[52] U.S. Cl. .................................. 568/697; 568/699; 203/91
[58] Field of Search ................. 568/697, 699; 203/91

[56] References Cited

U.S. PATENT DOCUMENTS

| 3,119,766 | 1/1964 | Voltz | 568/697 |
| 3,726,942 | 4/1973 | Louder | 568/697 |
| 3,940,450 | 2/1976 | Lee | 568/697 |
| 4,020,114 | 4/1977 | Rescalli et al. | 568/697 |

FOREIGN PATENT DOCUMENTS

| 957000 | 4/1964 | United Kingdom | 568/697 |
| 1176620 | 1/1970 | United Kingdom | 568/697 |

OTHER PUBLICATIONS

Horsley, Azeotropic Data-III, Adv. in Chem. Series 116, Amer. Chem. Soc., Washington, D.C., 1973, pp. 80, 594, 601, 615–622, 626–628.

*Primary Examiner*—Howard T. Mars
*Attorney, Agent, or Firm*—Gilbert L. Wells

[57] ABSTRACT

Process for the preparation of pure methyl tert.-butyl ether. Isobutene or isobutene-containing hydrocarbon mixtures are reacted with methanol in a molar ratio of 1:1 to 1:2 in the liquid phase at temperatures of between 30° and 100° C. on sulfonated, strongly acidic, macroporous organic ion exchange resins. After separation of the unreacted hydrocarbons, the reaction mixture is distilled under pressure; the methanol-containing distillate formed during the distillation is recycled into the zone of the reaction between methanol and isobutene; and pure methyl tert.-butyl ether is withdrawn from the sump of the distillation column.

5 Claims, 1 Drawing Figure

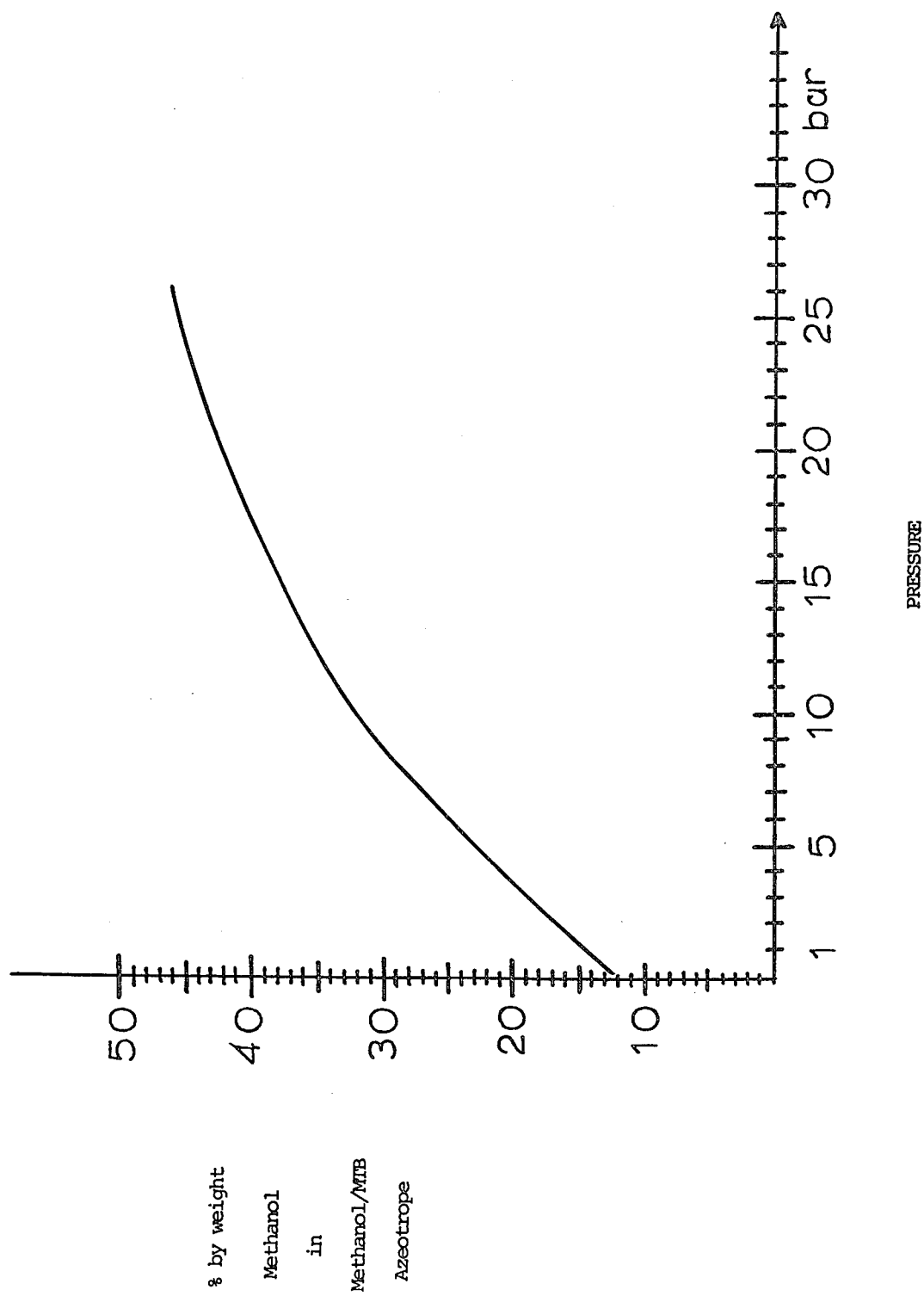

PROCESS FOR PREPARING PURE METHYL TERT.-BUTYL ETHER

CROSS-REFERENCE TO A RELATED APPLICATION

This is a continuation of application Ser. No. 810,878, filed June 28, 1977, now abandoned.

Applicants claim priority under 35 USC 119 for application No. P 26 29 769.8 filed July 2, 1976 in the Patent Office of the Federal Republic of Germany.

BACKGROUND OF THE INVENTION

The field of the invention is the preparation of methyl tert.-butyl ether (MTB) by the catalytic addition of methanol to isobutene. The state of the art of this preparation may be ascertained by reference to U.S. Pat. Nos. 1,968,601; 2,197,023; 2,282,462; 2,480,940; 2,922,822; 3,121,124; 3,135,807; 3,482,952; 3,718,701 and 3,906,054; the disclosures of which are incorporated herein.

In the catalytic addition of methanol to isobutene, the catalysts employed are acids, such as, for example, $H_2SO_4$, as disclosed in U.S. Pat. No. 1,968,601, Lewis acids, such as, for example $BF_3$ as disclosed in U.S. Pat. No. 2,197,023, platinum metal salts, such as disclosed in U.S. Pat. No. 3,718,701, or also heterogeneous catalysts. Suitable heterogeneous catalysts are, in addition to phosphoric acid on kieselguhr (U.S. Pat. No. 2,282,462), phosphorous-modified zeolites (U.S. Pat. No. 3,906,054), bismuth molybdate and salts of phosphomolybdic acid (U.S. Pat. No. 3,135,807), especially sulfonated organic resins (e.g. U.S. Pat. No. 2,480,940). This group also includes sulfonated polystyrene resins cross-linked with divinylbenzene (U.S. Pat. No. 2,922,822), which can have a gel-type consistency or which can exhibit a sponge structure with macropores to enlarge the surface area and thus to increase the reaction velocity (German Pat. No. 1,224,294, Example 8; U.S. Pat. No. 3,482,952).

In general, the isobutene utilized for the reaction is not pure; rather, isobutene-containing hydrocarbon mixtures are employed from which the isobutene is made to react selectively, inasmuch as the reaction of isobutene with methanol takes place substantially more rapidly than the reaction of the remaining component present in the mixture with methanol.

Accordingly, isobutene can be reacted selectively with methanol not only in a mixture with saturated hydrocarbons, but also in a mixture with unsaturated hydrocarbons, such as propene, butenes (U.S. Pat. No. 3,121,124), or also butadiene (German Published Application DOS No. 2,521,673).

The selectively of the MTB formation is the higher, when using isobutene-containing hydrocarbon mixtures as well as with the use of pure isobutene, the lower the reaction temperature lies. Also the equilibrium of the exothermic ether formation is enhanced by low temperatures. However, with a decreasing temperature, the reaction velocity is reduced so that it becomes increasingly more difficult to attain an approximately complete isobutene conversion—in correspondence with the more favorable equilibrium. Thus, it is hardly possible to operate below the temperature range of 50°-60° C., for example, when using the macroporous, sulfonated organic resins especially effective among the heterogeneous catalysts, if it is desired to attain the thermodynamic equilibrium still within practically feasible contact times. With the equimolar utilization of isobutene and methanol, conversion rates of merely up to at most 92% can be obtained in this connection (DOS No. 2,521,963, page 2).

However, an isobutene conversion which is so inadequate is unsatisfactory with respect to the utilization of the raw material as well as with regard to the quality of the residual hydrocarbons remaining with the use of, for example, a cracked $C_4$ hydrocarbon cut.

One possibility for completing the isobutene conversion is an increase in the amount of methanol supplied to the reaction. However, with this mode of operation, the MTB thus produced contains considerable quantities of methanol, and extraordinary difficulties are encountered in separating the methanol from the MTB on account of the formation of an azeotrope with a high MTB content. Thus, in order to separate methanol from MTB, for example, suggestions have been advanced to conduct an extractive distillation with dimethyl sulfoxide or also a water washing process (DOS No. 2,246,004; Japanese Laid-Open Application No. 73-00509).

SUMMARY OF THE INVENTION

It is an object of this invention to provide a process which makes it possible to produce pure methyl tert.-butyl ether in a simple manner in spite of a considerable excess of methanol during the reaction with isobutene.

This object has been attained by a process for the preparation of pure methyl tert.-butyl ether by reacting isobutene or isobutene-containing hydrocarbon mixtures with methanol in a molar ratio of 1:1 to 1:2 in the liquid phase at temperatures of between 30° and 100° C. on sulfonated, strongly acidic, macroporous organic ion exchange resins. The process is characterized in that, after separation of the unreacted, gaseous hydrocarbons, the reaction mixture is distilled under pressure; the methanol-containing distillate formed during the distillation is recycled into the zone of the reaction between methanol and isobutene; and pure methyl tert.-butyl ether is withdrawn from the sump of the distillation column.

BRIEF DESCRIPTION OF THE DRAWING

The FIGURE of the drawing appended herewith is an X-Y plot of methanol in the distillate (methanol/MTB azeotrope) in percent by weight versus the bar value of pressure used during the distillation.

DESCRIPTION OF THE PREFERRED EMBODIMENTS

It has been found surprisingly that during the distillation of a methanol/MTB mixture the methanol proportion in the distillate (azeotrope) rises with increasing pressure. It is possible thereby to return the distillate into the reaction zone without recirculating unreasonably large amounts of distillate. Even with an increase of the pressure to merely 1.3 bar, which is possible even in any kind of technically customary normal-pressure column, the methanol proportion in the distillate is increased from 14% to 14.7%. Already by this minor increase, the amount of the distillate to be recycled can be reduced by 5%. The pressure should not exceed 30 bar in view of the fact that the costs for the construction of the column rise with increasing pressure. The expenses incurred with higher pressures are no longer compensated for by the increased yield. A particularly economical pressure range is between 5 and 20 bar.

The ratio of methanol to isobutene is in the range of 1:1 to 2:1. If the value of 1:1 is exceeded in the downward direction, the utilization of the isobutene raw material is entirely unsatisfactory; when exceeding the value of 2:1, the process becomes uneconomical due to the increasing expense for the methanol separation. Good results can be achieved with a ratio of methanol to isobutene of 1.2:1 to 1.5:1. Advantageously, the excess of methanol is chosen to be no larger than necessary for obtaining an extensive isobutene conversion under selective conditions.

The reaction temperatures for the reaction of isobutene with methanol range between 30° and 100° C. With reduced temperatures, the reaction velocity is reduced, but the reaction equilibrium is shifted in the direction toward a complete conversion of the starting materials. In general, to obtain a satisfactory reaction velocity, the process is carried out in a temperature range of 50°–100° C. It proved to be especially advantageous to maintain the reaction temperature in the first two thirds of the catalyst bed between 70° and 100° C. and in the last third at 30°–50° C. Thereby, a rapid reaction is obtained in the first third of the catalyst bed, while the reaction equilibrium in the last third is shifted toward complete conversion. The advantage of this mode of operation resides in that, in spite of brief reaction times, an advantageous reaction equilibrium can be attained.

The separation of the unreacted hydrocarbons from the reaction mixture before the pressure distillation takes place by means of distillation as disclosed in German Published Applications DOS Nos. 1 934 422 and 2 535 471.

An inversely proportional relationship exists between the methanol proportion in the distillate of the pressure distillation and the quantity of distillate to be recycled into the reaction zone. The relationship, shown in the drawing, between the pressure utilized during the distillation and the proportion of methanol in the distillate (methanol/MTB azeotrope) permits the selection of suitable azeotrope compositions over a very wide range and/or makes it possible to determine the suitable distillation pressure at a desired azeotrope (=distillate) composition. The level to which the methanol proportion in the distillate (=azeotrope) is increased by raising the distillation pressure is dependent on purely economical considerations. An increase in the costs for the pressure column must be weighed against a reduction of the energy costs for the distillation, the decrease in the amount of heat of condensation to be removed, a favorably increased temperature level to remove the heat, and particularly the reduction in reactor size for a specific MTB quantity produced in this way. The last-mentioned advantage is of particular importance, since the MTB recycled with the distillate not only requires additional reactor space but also reduces, due to the dilution effect, the MTB formation velocity which in each case is proportionally dependent in a first approximation on the isobutene and methanol concentrations, and this makes it extraordinarily difficult to complete the conversion. Consequently, the molar ratio between methanol and isobutene, as well as the pressure during the distillation are suitably chosen so that the recycled amount of distillate is less than 30% of the amount of MTB produced in the pure state. The amount of distillate to be recycled can be calculated in accordance with the following formula:

$$R = \frac{100\,V - U - 0.01\,M \cdot \left(\frac{10{,}000}{I}\right) \cdot (1 + 0.01\,M) \cdot 1.751}{2.751 \cdot 0.01\,U \cdot 0.01\,A}$$

wherein
- R = percent by weight of recycled quantity of distillate, based on MTB obtained in the pure state,
- V = molar ratio of methanol:isobutene in the starting mixture,
- U = percent of isobutene conversion,
- M = percent by weight of methanol in the separated (unreacted) residual hydrocarbons,
- I = percent by weight of isobutene in the hydrocarbon starting mixture,
- A = percent by weight of methanol in the recycled distillate.

The reactor charged with strongly acidic ion exchanger and useful in the present invention is disclosed in German Published Application DOS No. 2 246 004.

Specific examples of the macroporous, sulfonated polystrene crosslinked with divinylbenzene include, but are not limited to Amberlyst 15, Amberlite IR 200, Amberlite IR 252, Dowex 50, Lewatit SPC 108, Lewatit 118, Permutit RSP 100, Permutit RSP 120.

The pressure distillation columns useful in the present invention are disclosed in Ullmanns Encyclopädie der Technischen Chemie, 4th ed., vol. 2 (1972), pp. 489–545.

With the present invention, a process has been discovered for the first time which makes it possible in a simple manner to produce MTB at high reaction velocities and good conversion rates.

EXAMPLE 1

1,095 kg./h of a $C_4$ cut containing 45% isobutene, 290 kg./h. of methanol, and 314 kg./h. of recycled azeotrope containing 100 kg. of methanol, 212 kg of MTB, and 2 kg. of $C_4$ cut are passed through a reactor charged with 1 m³ of a strongly acidic ion exchanger (macroporous, sulfonated polystyrene crosslinked with divinylbenzene) and from which the thus-produced heat of reaction can be thoroughly removed by the installation of suitable cooling devices. The amount charged corresponds to a 1.38-fold molar excess of methanol, based on isobutene.

At a maximum temperature of about 80° C. in the reactor bed, 98.6% of the isobutene is reacted. In addition to MTB, in correspondence with the water dissolved in the $C_4$ cut, other reaction products are 1.5 kg./h. of tert.-butanol and 1.0 kg./h. of a $C_8/C_{12}$ olefin mixture (di- and trimerization products of isobutene). Accordingly, in total, the following components are discharged from the reactor:

611.0 kg./h.—$C_4$ Hydrocarbons
113.5 kg./h.—MeOH
972.0 kg./h.—MTB
1.5 kg./h.—tert.-Butanol
1.0 kg./h.—$C_8/C_{12}$ Olefin mixture The reaction product is then introduced into a pressure column to separate the unreacted $C_4$ hydrocarbons where at the head of the column 608.5 kg./h. of $C_4$ hydrocarbons and 12 kg. of methanol are withdrawn (methanol forms an azeotrope with the $C_4$ hydrocarbons under the distillation conditions). The remaining products are withdrawn from the sump of the column and passed on to a second pressure column operated under a pressure of 10 bar. With a pressure of 10 bar, the MTB-methanol azeotrope contains 32% of methanol. Consequently, at the head of the column, at a boiling temperature of 130° C., an azeotropic mixture is withdrawn consisting of 100 kg. of methanol, 212 kg. of MTB, and 2 kg. of $C_4$ hydrocarbons; consequently, the following products are discharged from the sump:

0.5 kg./h.—$C_4$ Hydrocarbons
1.5 kg./h.—tert.-Butanol
1.0 kg./h.—$C_8/C_{12}$ Olefin mixture
1.5 kg./h.—Methanol
760.0 kg./h.—MTB As a result, the amount of the distillate (MTB-methanol azeotrope) which must be recycled is only 41.1% (R=41.1) related to the MTB obtained in the sump. If the second column were operated without pressure, whereby merely 14% of methanol accumulates in the MTB-methanol azeotrope, then R is 197.5. This would lead to a higher energy consumption and to a reduction in the Conversion (shorter residence time and reduction in the concentration of the reactants).

EXAMPLE 2

968.0 kg./h. of a $C_4$ cut containing 45% isobutene, 257 kg./h. of methanol, and 122 kg./h. of recycle azeotrope containing 65 kg. of MTB, 55.5 kg. of methanol, and 1.5 kg. of $C_4$ hydrocarbons are passed through a reactor charged with 1 m$^3$ strongly acidic ion exchanger (macroporous, sulfonated polystyrene crosslinked with divinylbenzene) and from which the thus-produced heat of reaction can be thoroughly removed by the installation of suitable cooling devices. The amount charged corresponds to a 1.25 molar excess of methanol, based on isobutene.

At a maximum temperature of about 70° C. in the reactor bed, 98.5% of the isobutene is converted. In addition to MTB, there are obtained, in correspondence with the water dissolved in the $C_4$ cut, 1 kg./h. of tert.-butanol and 1 kg./h. of $C_8/C_{12}$ olefin mixture (di- and trimerization products of isobutene), so that, in total, the following components are discharged from the reactor:

539.0 kg./h.—$C_4$ Hydrocarbons
67.0 kg./h.—Methanol
739.0 kg./h.—MTB
1.0 kg./h.—tert.-Butanol
1.0 kg./h.—$C_8/C_{12}$ Olefin mixture The reaction product is then introduced into a pressure column; the distillate withdrawn therefrom consists of 537 kg./h. of unreacted $C_4$ hydrocarbons together with 10.5 kg./h. of methanol which, under the ambient pressure conditions, forms an azeotrope with the $C_4$ hydrocarbons. The following components are discharged from the sump of the column:

2.0 kg./h.—$C_4$ Hydrocarbons
739.0 kg./h.—MTB
56.5 kg./h.—Methanol
1.0 kg./h.—tert.-Butanol
1.0 kg./h.—$C_8/C_{12}$ Olefin mixture This mixture is fed to a second pressure column, the pressure of which is set to be 25 bar. At a boiling temperature of 171° C., 120.5 kg./h. of an MTB-methanol azeotrope, containing 46% methanol, is withdrawn from the head of this column together with 1.5 kg./h. of $C_4$ hydrocarbons.

As the sump product, 674 kg./h. of MTB together with 0.5 kg. of $C_4$ hydrocarbons, 1 kg./h. of tert.-butanol, 1 kg./h. of $C_8/C_{12}$ olefin mixture, and 1 kg. of methanol are discharged from the column. Consequently, the amount of distillate, which must be recycled is 18% (R=18), related to the obtained pure MTB.

EXAMPLE 3

If the MTB-methanol azeotrope to be recycled is distilled off in a normal pressure column which can be operated under a pressure of 1.35 bar, then it is necessary to operate with a molar excess of methanol, based on the isobutene, 1.1:1, in order to avoid the recycling of an excessive amount of MTB.

A reactor containing 1 m$^3$ of strongly acidic ion exchanger (macroporous, sulfonated polystyrene crosslinked with divinylbenzene) is charged with 624 kg./h. of a $C_4$ cut containing 45% isobutene, 161.5 kg./h. of methanol, and 106 kg./h. of recycled product consisting of 1.5 kg. of $C_4$ hydrocarbons, 15.5 kg. of methanol, and 89 kg. of MTB. While in the first portion of the reactor a maximum catalyst temperature of 70° C. is maintained, the temperature in the second portion is maintained at 40° C. to increase the conversion by equilibrium adjustment, so that an isobutene conversion of 96% is obtained. With a reactor temperature of 70° C. at the end of the catalyst bed, one could merely attain an isobutene conversion of 94%. The reaction product formed per hour, containing:

354.5 kg.—$C_4$ Hydrocarbons
23.0 kg.—Methanol
512.0 kg.—MTB
0.5 kg.—tert.-Butanol
1.5 kg.—$C_8/C_{12}$ olefin mixture is introduced into the first column where 352.5 kg./h. of $C_4$ hydrocarbons and 7 kg./h. of methanol are withdrawn at the head of the column, while the following components are discharged from the sump:

2.0 kg./h.—$C_4$ hydrocarbons
16.0 kg./h.—Methanol
512.0 kg./h.—MTB
0.5 kg./h.—tert.-Butanol
1.5 kg./h.—$C_8/C_{12}$ Olefin mixture.

This mixture is introduced into the second column operated at 1.35 bar, where 104.5 kg./h. of MTB-methanol azeotrope, containing 15.5 kg. (corresponding to 14.7%) of methanol, is withdrawn from the head of the column, together with 1.5 kg./h. of $C_4$ hydrocarbons. From the sump is discharged 423 kg./h. of MTB and, as the by-products;

0.5 kg./g.—$C_4$ Hydrocarbons
0.5 kg./h.—Methanol
0.5 kg./h.—tert.-Butanol
1.5 kg./h.—$C_8/C_{12}$ Olefin mixture The amount of distillate, which has to be recycled is 24.8% (R=24.8%), related to the obtained pure MTB.

We claim:

1. A process for the preparation of pure methyl tert.-butyl ether comprising reacting isobutene or isobutene-containing $C_4$ hydrocarbon mixtures with methanol in a molar ratio of said methanol to said isobutene of 1:1 to 2:1 in the liquid phase at temperatures of between about 30° and 100° C. in a reaction zone on sulfonated strongly acidic, macroporous organic ion exchange resins; separating and removing unreacted $C_4$ hydrocarbons from the reaction mixture and leaving separated reaction mixture, distilling said separated reaction mixture under pressure of 1.3–30 bar in a distillation column to produce an azeotrope of methanol and methyl tert.-butyl ether as the distillate thereof and pure methyl tert.-butyl ether from the sump thereof, recycling said distillate formed during the distillation into said zone of the reaction between methanol and isobutene; and withdrawing said pure methyl tert.-butyl ether from the sump of the distillation column.

2. The process of claim 1, wherein the reaction mixture is distilled under a pressure of 5–20 bar.

3. The process of claim 1, wherein the amount of recycled distillate is chosen, in accordance with the formula:

$$R = \frac{100\,V - U - 0.01\,M \cdot \left(\frac{10{,}000}{I}\right) \cdot (1 + 0.01\,M) \cdot 1.751}{2.751 \cdot 0.01\,U \cdot 0.01\,A}$$

wherein
  R = percent by weight of recycled quantity of distillate, based on methyl tert.-butyl ether obtained in the pure state,
  V = molar ratio of methanol:isobutene in the starting mixture,
  U = percent of isobutene conversion,
  M = percent by weight of methanol in the separated, unreacted residual hydrocarbons,
  I = percent by weight of isobutene in the hydrocarbon starting mixture,
  A = percent by weight of methanol in the recycled distillate,
so that less than about 30% of distillate is recycled, based on the amount of methyl tert.-butyl ether produced in the pure state.

4. The process of claim 1, wherein the temperatures of said reaction zone are between 50° and 100° C.

5. The process of claim 1, wherein the temperatures in the first two thirds of said reaction zone are between 70° and 100° C. and the temperatures in the last one third of said reaction zone are between 30° and 50° C.

* * * * *